(12) United States Patent
Nemard

(10) Patent No.: US 9,072,653 B2
(45) Date of Patent: Jul. 7, 2015

(54) MEDICATION SUPPORT CASE HAVING REMOVABLE AND FORM-FITTING SUPPORT

(71) Applicant: Linda Nemard, Brooklyn, NY (US)

(72) Inventor: Linda Nemard, Brooklyn, NY (US)

( * ) Notice: Subject to any disclaimer, the term of this patent is extended or adjusted under 35 U.S.C. 154(b) by 0 days.

(21) Appl. No.: 13/861,916

(22) Filed: Apr. 12, 2013

(65) Prior Publication Data

US 2013/0277262 A1 Oct. 24, 2013

Related U.S. Application Data

(60) Provisional application No. 61/637,036, filed on Apr. 23, 2012.

(51) Int. Cl.
| | | |
|---|---|---|
| *A61J 1/03* | (2006.01) | |
| *B65D 25/10* | (2006.01) | |
| *B65D 23/10* | (2006.01) | |
| *A61B 19/02* | (2006.01) | |
| *A45C 13/02* | (2006.01) | |

(52) U.S. Cl.
CPC ............... *A61J 1/03* (2013.01); *B65D 23/102* (2013.01); *A45C 2013/026* (2013.01); *A61B 19/0264* (2013.01); *A61B 2019/0209* (2013.01); *A61B 2019/0244* (2013.01); *A61B 2019/0278* (2013.01)

(58) Field of Classification Search
CPC ............ B65D 25/102; B65D 81/3823; B65D 81/3834; A61J 1/03; A45C 3/02; A45C 13/02
USPC ......... 206/223, 282, 366, 438, 477, 483, 490, 206/521, 523–524, 541, 549, 569–570, 775, 206/781–782; 220/528–530; 190/109–110
See application file for complete search history.

(56) References Cited

U.S. PATENT DOCUMENTS

| | | | | |
|---|---|---|---|---|
| 1,712,686 | A * | 5/1929 | Bornmann | 206/480 |
| 2,648,366 | A * | 8/1953 | Higbee et al. | 206/570 |
| 3,088,584 | A * | 5/1963 | Kozikowski | 206/572 |
| 3,181,693 | A * | 5/1965 | Freistat | 206/523 |
| 3,777,882 | A * | 12/1973 | McIntyre | 206/370 |
| 4,106,597 | A * | 8/1978 | Shook et al. | 190/110 |
| 4,303,610 | A * | 12/1981 | Sardisco et al. | 422/430 |
| 4,461,332 | A * | 7/1984 | Parkhurst | 150/112 |
| 4,569,082 | A * | 2/1986 | Ainsworth et al. | 383/3 |
| 4,763,791 | A * | 8/1988 | Halverson et al. | 206/570 |
| 4,836,374 | A * | 6/1989 | Hutchins et al. | 206/373 |

(Continued)

*Primary Examiner* — Bryon Gehman
*Assistant Examiner* — Brijesh V. Patel
(74) *Attorney, Agent, or Firm* — Daniel Boudwin; Global Intellectual Property Agency LLC

(57) ABSTRACT

A medication carrying case is provided having a first and second half hingedly attached and removably securable to one another along a removable line of connection. Within the interior of the carrying case halves is a removable medication support member having a plurality of surface depressions along its upper surface and a case connector along its underside surface. Each support member secures to an inner surface of the case halves and is designed to fit therewithin. The depressions are adapted to form-fittingly secure pill bottles, medication vials, syringes, and other medical supplies therein. Further provided over each depression is a securing strap, which is connected to the member upper surface along one end and is removably attachable across the depression along its second end. In this way, the carrying case provides a medication holder and support that securely holds medication and accessories on the go.

5 Claims, 3 Drawing Sheets

(56) References Cited

U.S. PATENT DOCUMENTS

| | | | | |
|---|---|---|---|---|
| 5,010,988 A | * | 4/1991 | Brown | 190/104 |
| 5,040,678 A | * | 8/1991 | Lenmark et al. | 206/443 |
| 5,052,555 A | * | 10/1991 | Harmon | 206/315.11 |
| 5,096,030 A | * | 3/1992 | Espinosa et al. | 190/108 |
| 5,207,303 A | * | 5/1993 | Oswalt et al. | 190/108 |
| 5,579,916 A | * | 12/1996 | Manko | 206/581 |
| 6,000,509 A | * | 12/1999 | Chisholm | 190/109 |
| 6,036,019 A | * | 3/2000 | Silverman | 206/545 |
| 6,119,858 A | * | 9/2000 | Davidson | 206/315.11 |
| 6,152,303 A | * | 11/2000 | Ducote et al. | 206/703 |
| 6,241,090 B1 | * | 6/2001 | Kaplinsky | 206/315.11 |
| 6,244,400 B1 | * | 6/2001 | Bowers | 190/110 |
| 6,467,619 B1 | * | 10/2002 | Leen et al. | 206/421 |
| 6,779,665 B2 | * | 8/2004 | Bolanos | 206/569 |
| 6,874,628 B2 | * | 4/2005 | Hammill | 206/317 |
| 6,981,593 B1 | * | 1/2006 | Klodt | 206/541 |
| 7,565,979 B1 | | 7/2009 | Gibson | |
| 7,926,661 B2 | * | 4/2011 | Beeman | 206/572 |
| 8,006,846 B2 | | 8/2011 | Robertson | |
| 8,167,131 B1 | * | 5/2012 | Anderson | 206/575 |
| 2001/0015332 A1 | * | 8/2001 | Flynn | 206/523 |
| 2006/0254950 A1 | | 11/2006 | Barlog et al. | |
| 2009/0010575 A1 | | 1/2009 | Sanka | |

* cited by examiner

MEDICATION SUPPORT CASE HAVING REMOVABLE AND FORM-FITTING SUPPORT

CROSS REFERENCE TO RELATED APPLICATION

This application claims the benefit of U.S. Provisional Application No. 61/637,036 filed on Apr. 23, 2012, entitled "Remedy Carry Bag." The above identified patent application is herein incorporated by reference in its entirety to provide continuity of disclosure.

BACKGROUND OF THE INVENTION

1. Field of the Invention

The present invention relates to medical carrying cases. More specifically, the present invention pertains to a new and unique carrying case for personal medication items, wherein a removable medication tray is provided for organizationally arranging pill bottles, vials, and related supplies with a form-fitting case insert having retaining straps to support the items within the interior of the case.

Many individuals require doses of medication throughout the day to maintain their health or to treat various ailments. Some of these individuals require an assortment of medication that is administered in pill form or more direct forms, such as insulin injections or the like. Organizing and transporting medication in pill or vial form can be a bothersome task, where the user must store the items appropriately and in such a manner to allow for later retrieval, while at the same time preventing the items from spilling, interacting with one another, degrading, or becoming misplaced.

When traveling, organization is of the utmost priority, as the medication must be available and in a known location to allow for ready administration of correct medication types and dosages in a timely. Self-administered medication requires a careful eye for correct dosages, which requires taking proper measures to adequately organize pill containers, vials, and other medication such that their labels are visible and each medication type is readily accessible when required.

Patients therefore require organized and efficient access to their medication so they can administer the medication on the appropriate schedule, while also making the medication available in the event of an emergency situation. Lazily storing the medication in a purse or storage bag can lead to missing pill bottles and instances where the pills may be inadvertently left out of the travel bag altogether. These situations introduce a patient to potential health risks and even life threatening conditions if daily and regular medication is required for the patient to remain healthy throughout each day. Even in a less severe case, those patients who consistently miss their dosages of medication can introduce long term problems that can hamper their recovery and their overall treatment effectiveness, while also introducing variables that may not be considered by healthcare providers assessing the patient's progress with a given medication type.

The present invention provides a new and unique medication carrying device that employs a removable set of preformed support structures within the interior of the case. The support structures comprise a raised body and an upper surface having a plurality of depressions therealong for form-fitting to the exterior features of typical pill bottles, vials, and medical devices known in the art. The medication is supported within the depressions and further secured therein by way of removable strap retainment means, which secure the items therein and prevent relative movement within the case or dislodgment from within the depressions. Overall, the device improves the ability to organize medication and necessary supplies while traveling, while providing an efficient manner in which to support the items for the user to quickly recognize and retrieve necessary items as desired.

2. Description of the Prior Art

Devices have been disclosed in the prior art that relate to medical carrying cases. These include devices that have been patented and published in patent application publications, and generally relate to carrying cases and briefcases having particular internal structure for supporting different medication and treatment items while on the go. The following is a list of devices deemed most relevant to the present disclosure, which are herein described for the purposes of highlighting and differentiating the unique aspects of the present invention, and further highlighting the drawbacks existing in the prior art.

Specifically, U.S. Pat. No. 7,565,979 to Gibson discloses a pill holding device that includes a housing case having two folding and connectable walls forming the case structure and an interior comprising a plurality of loops that extend from the inner surfaces of the case walls to secure medication bottles therein. The loops comprise stretchable material to form over the outer surface of the medication bottles, securing the same to the inner walls of the case. A lowermost pill case is further disposed within the case interior for storing loose pills and other items. While disclosing a novel carrying case for medication and their containers, the Gibson device fails to disclose the novel arrangement of the present invention, which provides a formed interior structure that accepts medication bottles therein and secures them within depressions by way of a retaining strap.

U.S. Pat. No. 8,006,846 to Robertson is another such device that discloses a portable carrying case for holding medication and medical vials while traveling. The case includes a securable lid and an interior volume, wherein a plurality of upstanding divider walls are disposed along the case interior surface for positioning vials and medication bottles. An elastic cord is slidable through aligned holes in upstanding divider walls to secure the medication between the divider walls and to prevent the medication from moving or dislodging therefrom. Similar to the Gibson device, the Robertson device fails to disclose the novel arrangement of the present carrying case interior, which includes a molded structure having a plurality of depressions for supporting medication bottles and supplies.

Finally, U.S. Patent Application Publication No. 2009/0010575 to Sanka and 2006/0254950 to Barlog disclose medication organizers utilizing a case or similar structure, whereby a plurality of medication vials or containers are organized for a user such that their organized retrieval as facilitated while traveling. These devices, while disclosing unique carrying cases directed at medication, do not disclose the carrying case elements of the present invention, which contemplates an internal arrangement having defined apertures and depressions therein for supporting specific or generic medicine bottles and similar supplies.

The present invention provides a new and novel medical carrying case having removable pill bottle and vial support members within the interior of the case. The support members include a defined structure having depressions along their upper surface to support medication bottles, vials, and other supplies therein, while a securement strap is positioned thereover. It is submitted that the present invention substantially diverges in design elements from the prior art, and consequently it is clear that there is a need in the art for an improvement to existing medical carrying case devices. In this regard the instant invention substantially fulfills these needs.

SUMMARY OF THE INVENTION

In view of the foregoing disadvantages inherent in the known types of medical carrying cases now present in the prior art, the present invention provides a new carrying case having removable medication support members therein, which can be utilized for providing convenience for the user when transporting medication and associated supplies within a case while on the go.

It is therefore an object of the present invention to provide a new and improved medical carrying case that has all of the advantages of the prior art and none of the disadvantages.

It is another object of the present invention to provide a medical carrying case that supports medication using a form-fitting, removable member that can be designed to support pill bottles, vials, syringes, and other medical supplies or equipment using specifically designed depressions and a securement strap thereover.

Another object of the present invention is to provide a medical carrying case having a first and second half forming an interior volume, wherein each half supports a removable medication support member therein.

Yet another object of the present invention is to provide a medical carrying case that provides a patient or medical professional with an organized carrying case for medication and supplies, wherein the articles are snugly supported within the form-fitted depressions of the removable support members within the interior of the case.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
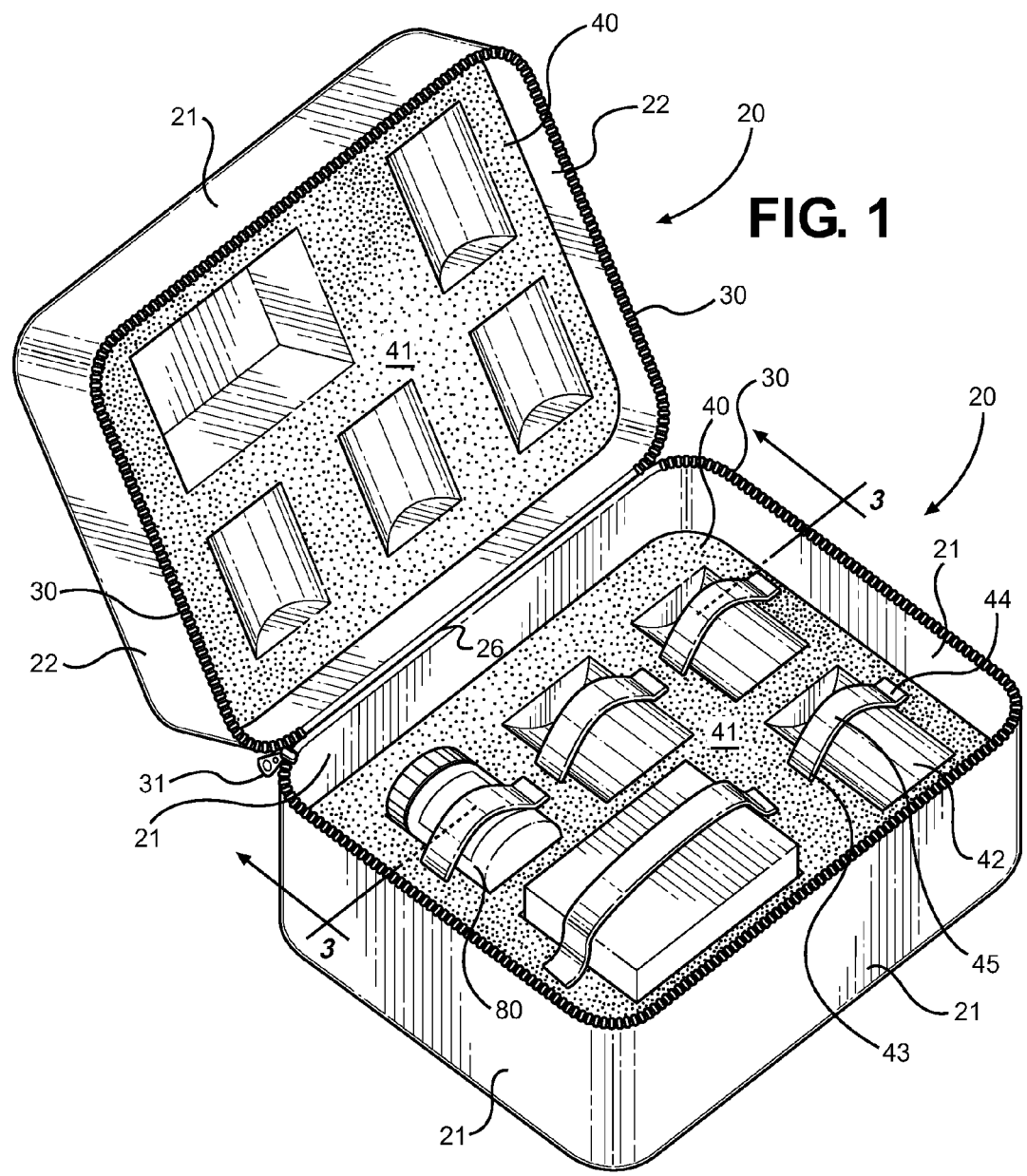
FIG. 1 shows an overhead perspective view of the carrying case in an open position, highlighting the removable interior support members and their surface depressions for supporting various medication and medical supplies.

Reference is made herein to the attached drawings. Like reference numerals are used throughout the drawings to depict like or similar elements of the medical carrying case. For the purposes of presenting a brief and clear description of the present invention, the preferred embodiment will be discussed as used for securely supporting and organizing medication and supplies within a carrying case while on the go. The figures are intended for representative purposes only and should not be considered to be limiting in any respect.

Referring now to FIG. 1, there is shown an overhead perspective view of the medical carrying case of the present invention in an open configuration. The case comprises a first and second half 20, wherein the halves 20 are hingedly attached 26 along one edge and removably securable to one another along a zippered 31 line of connection 30 about the remaining edges. Each case half 20 comprises a substantially rectangular shape having upstanding sidewalls 21. The upstanding sidewalls are connected by a case half interior surface, which established an open interior volume within which to position at least one removable medication support member 40 or to support a permanent storage compartments for supporting supplies and other articles (not shown in FIG. 1).

The medication support member 40 consumes the majority of the case half 20 interior volume and is adapted to be secured therein along the case half interior surface by way of a removable connection means. The members 40 themselves comprise largely rectangular structures having a thickness, sidewalls, an upper surface 41, and an underside surface. Along the upper surface is disposed a plurality of depressions 42 that create cavities within which to position medication bottles, vials, and other articles related to medication. The depressions 42 are areas of the member thickness that has been removed, wherein the surface of the depression 42 conforms to the shape of a pill bottle or the like. Ideally the members 40 are comprised of an elastically deformable material that conforms to an article pressed into the depression 42 and follows its outer surface contours.

To secure each medical article 80 within a depression, the article is first pressed thereinto, whereafter a securement strap 45 is deployed over the article. The securement straps 45 comprise elongated strap members having a first end 43 and a second end 44, and preferably an elastic structure. The strap first end 43 is permanently secured to the upper surface 41 of the support member 40, while the strap second end 44 comprises a removable attachment means such as a strip of hook and loop fastener material to secure the second end to an opposite side of the depression 42. This draws the strap over an article 80 within the depression 42 and secures the article 80 therein, preventing dislodgement while in transit.

In one embodiment, one case half 20 supports a medication support member 40 and the opposing half 20 provides a plurality of internal pocket members along its interior surface for general storage of case articles. In this way, the case provides defined support for medication and medication-related items along one half and general storage along a second half.

Figure 2:
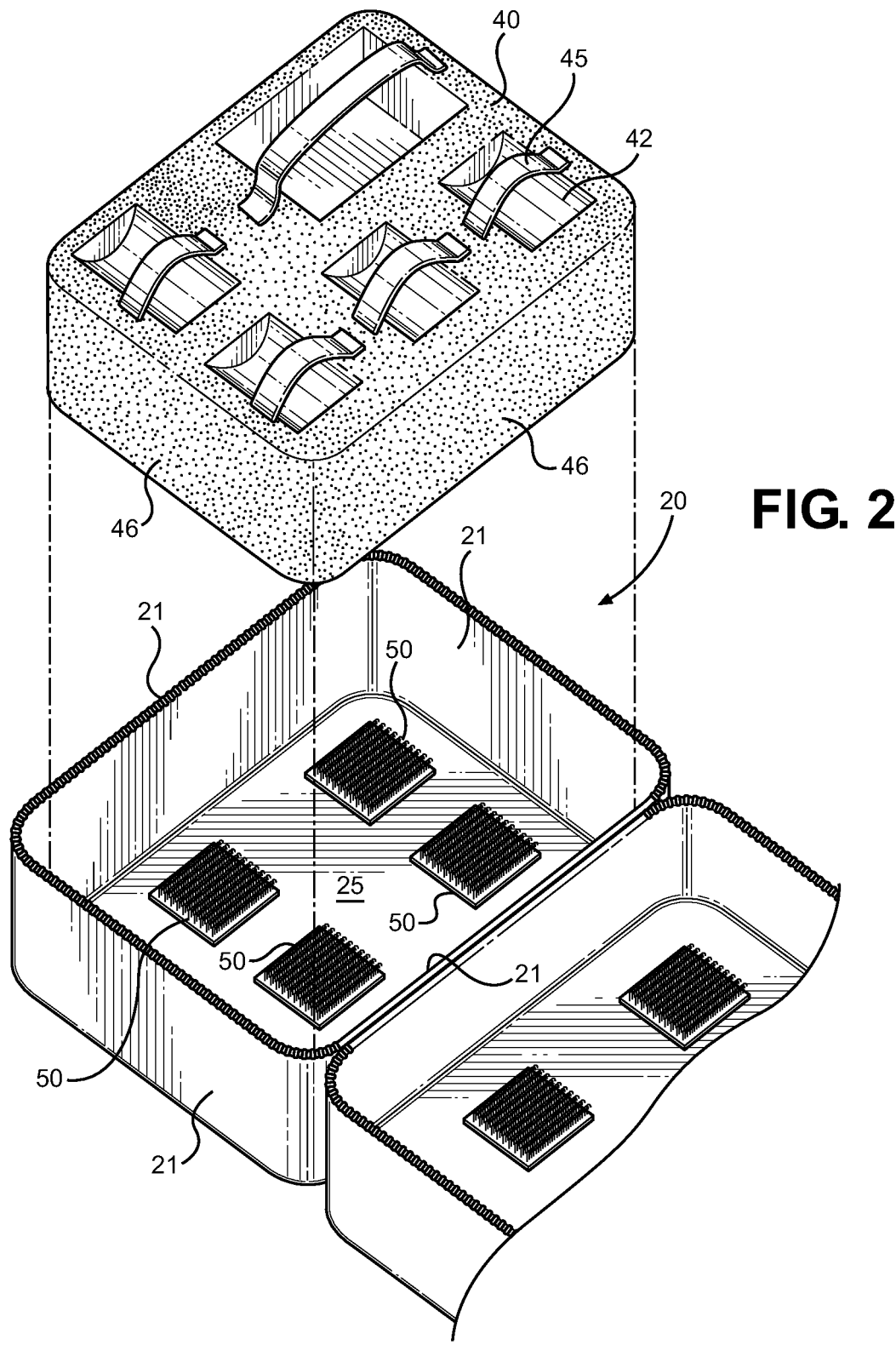
FIG. 2 shows a perspective view of the removable arrangement of the carrying case interior support members.

Referring now to FIG. 2, there is shown an exploded view of the present invention, wherein the interior support member 40 connection within the case halves 20 is shown. In this view, the case half interior surface 25 includes at least one member attachment means 50, which preferably comprise a plurality of hook and loop fastener strips for securing to corresponding strips along the underside surface of the removable member 40. The member 40 is positioned within the interior of the case half, wherein the member sidewalls 46 align with the case half sidewalls 21 and the thickness of the member 40 consumes the majority of the case half interior volume.

In this way, the present invention provides a medical case that can support different trays of medication or different types of removable arrangements within its interior, while offering an efficient means of securing the new arrangement within the case interior that does not require individual handling of the medication items one-by-one. A new or unique support member 40 may be positioned within the case interior and removed at a given destination, or the case can be utilized as a universal carrier for different support member arrangements, depending in the final destination of the carrier. This provides medical professionals and those in commercial settings with an easy and convenient way to pack medication in a carrying case for delivery or transport, wherein the arrangement of medication articles can be predetermined and simply "dropped-into" the case half for transport. Finally, the case may provide individual patients and users with a unique carrying case that firmly secures each item therein during transit.

Figure 3:
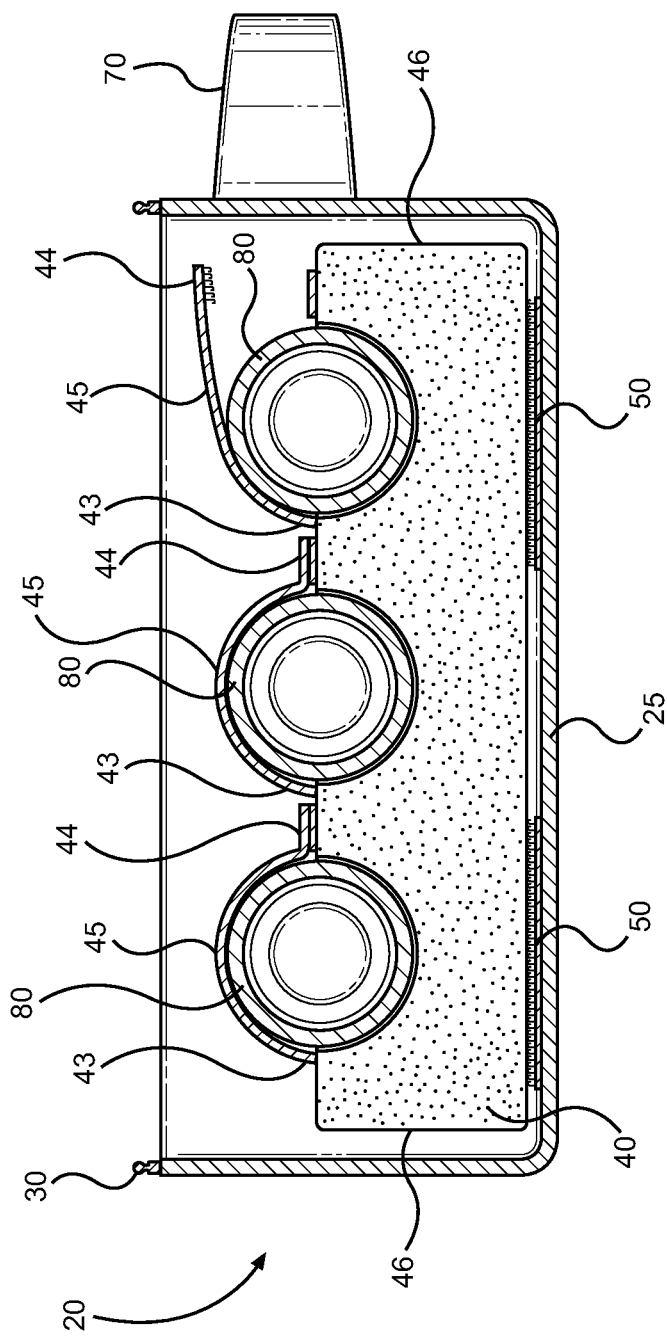
FIG. 3 shows a cross section through one of the carrying case halves, highlighting the construction of the support members and their connection to various medication bottles.

Referring now to FIG. 3, there is shown a cross section view of the case half in a working state, supporting a plurality of medication bottles 80 within its interior half 20. As visualized, the interior of the case half 20 supports the medication support member 40 along the case half interior surface 25. At least one attachment means 50 is disposed therealong to secure to corresponding attachment means on the underside surface of the removable member 40. Once installed, the sidewalls 46 of the removable member aligned with the case sidewalls, while the height of the case sidewalls allows for clearance of the medication items 80 stored within the surface depressions of the removable member upper surface.

When the items 80 are positioned within the depressions, the strap securement means 45 is positioned thereover. The strap first end 43 connects to the member upper surface and the strap second end 44 removably connects along an opposite side of the depression to secure the item therein. Once all items are positioned and secured, the case half 20 can be secured to the second half by way of its zippered line of connection 30. The user can then grasp the assembled carrying case by way of its handle 70 and transport the items and the case without fear of medication spillage or jostling within the carrying case interior.

It is contemplated that the removable support members may be constructed of different shapes and materials to provide a supportive and form-fitting structure for medication items. The members further provide a cushioning for the items therein, wherein glass jars and vials are prevented from clashing with other items secured within the case. To support the different items, it is contemplated that surface depressions having a rounded shape, a box shape, and other conformal contours may be provided, wherein specific applications of the case may call for different styles and shapes of support depressions. Finally, the case itself can take on different sizes and shapes, falling within the scope of the present disclosure.

It can be difficult to keep track of more than one or two medications at the same time, and people can easily lose or misplace their bottles or supplies. Packing up medicine before leaving the house can be time consuming and a hassle. If a person forgets one of his or her pills, he or she may have to return home for it, no matter what he or she was out doing. The present invention describes a carrying bag for medical supplies. The device comprises a zippered carrying case having two halves and interior support members specifically designed to fit different-sized medicine bottles. The members are preferably made from an elastic and compressible material, and securely hold and organize the medicine items contained therein. This provides a user with a convenient and hassle-free way to organize, store, and transport their medicine. The present invention can be used for transporting medical supplies to a doctor's appointment, while at work, or while traveling. This also prevents users from spending time gathering and organizing their medicine bottles and supplies.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A medication carrying case, comprising:
a first case half hingedly attached to a second case half;
each of said first case half and said second case half having upstanding sidewalls, a perimeter edge, and an open interior volume;
wherein said perimeter edge of said first case half is removably securable to said perimeter edge of said second case half;
at least one removable medication support member having an upper surface and an underside surface;
wherein said at least one removable medication support member is removably secured within said interior volume of said first case half or said interior volume of said second case half via fasteners disposed on said underside of said at least one removable medication support member;
said upper surface of at least one removable medication support member comprising at least one depression for supporting a medical item therein;
an elongated strap positioned over said at least one depression, said strap having a first strap end connected to said upper surface of said at least one removable medication support member along one side of said at least one depression, and a second strap end removably connected to said upper surface of said at least one removable medication support member along an opposite side of said depression.

2. The medication carrying case of claim 1, wherein said fasteners of said underside of said at least one removable medication support member comprises at least one strip of hook and loop fasteners.

3. The medication carrying case of claim 1, wherein said second strap end is removably connected to said upper surface of said at least one removable medication support member via hook and loop fasteners.

4. The medication carrying case of claim 1, wherein said at least one removable medication support member is composed of an elastic, compressible material.

5. The medication carrying case of claim 1, wherein each of said first case half and said second case half is rectangular in shape.

* * * * *